United States Patent [19]
Arita

[11] Patent Number: 5,990,195
[45] Date of Patent: Nov. 23, 1999

[54] DENTAL RESIN MATERIAL AND PROCESS FOR PRODUCING THE SAME

[75] Inventor: Akishi Arita, Tokyo, Japan

[73] Assignee: GC Corporation, Tokyo, Japan

[21] Appl. No.: 09/074,369

[22] Filed: May 8, 1998

[30] Foreign Application Priority Data

May 26, 1997 [JP] Japan ...................................... 9-149872

[51] Int. Cl.$^6$ ................................ A61C 5/08; C08K 3/34
[52] U.S. Cl. .......................... 523/116; 523/115; 523/209; 523/216; 524/493; 524/494; 528/502 C
[58] Field of Search ..................................... 523/115, 116, 523/209; 524/493, 494; 528/502 C

[56] References Cited

U.S. PATENT DOCUMENTS

| | | | |
|---|---|---|---|
| 4,297,266 | 10/1981 | Ibsen et al. | 523/115 |
| 4,859,716 | 8/1989 | Ibsen et al. | 523/116 |
| 5,356,951 | 10/1994 | Yearn et al. | 523/116 |

*Primary Examiner*—Andrew E. C. Merriam
*Attorney, Agent, or Firm*—Oblon, Spivak, McClelland, Maier & Neustadt, P.C.

[57] ABSTRACT

A dental resin material which is formed into a dental prosthesis by milling processing is disclosed, comprising an acrylic resin polymer containing from 20 to 70% by weight of an inorganic filler having a mean particle size of from 0.01 to 0.04 μm in diameter. A process for producing a dental resin material is also disclosed, which comprises polymerizing for curing a mixture comprising a combination of from 20 to 70% by weight of an inorganic filler having a mean particle size of from 0.01 to 0.04 μm in diameter, a methacrylate or acrylate monomer having at least one unsaturated double bond, and a heat polymerization initiator while elevating the pressure and heating under the conditions that the pressure is from 50 to 300 MPa and that the temperature is from 100 to 200° C. The dental resin material according to the invention has esthetics and mechanical properties suitable for dental prostheses such as inlays or crowns and being free from unpolymerized monomers, which is superior in machinability and can be suitably used for the preparation of dental prostheses by milling processing by means of a CAD/CAM device.

8 Claims, No Drawings ature of the invention

DENTAL RESIN MATERIAL AND PROCESS FOR PRODUCING THE SAME

FIELD OF THE INVENTION

The present invention relates to a dental resin material which is formed into a dental prosthesis by milling processing by means of a CAD/CAM (computer aided design/computer-aided manufacturing) device and to a process for producing the dental resin material.

BACKGROUND OF THE INVENTION

Hitherto, in the dental remedy, in the case of diseases where esthetics are required as in the case of inlays, crowns, and the like, filling restoration by a dental composite resin, or restoration by a dental prosthesis such as ceramic inlays, resin facing cast crowns, porcelain bonded facing cast crowns, and all ceramic crowns, has generally been employed.

The filling restoration by a dental composite resin is usually applied in the case of inlays and it is a restoration method in which a dental composite resin directly filled in a tooth cavity is polymerized for curing in the cavity by chemical polymerization or photo-polymerization. On the other hand, the restoration by a dental prosthesis is a restoration method in which after preparation of a cavity or preparation of an abutment tooth die, an impression (an tooth counterdie) is taken, a plaster model (a tooth duplicate) is prepared on a basis of the impression thus taken, a dental prosthesis is prepared on a basis of the model thus-prepared in the following manner, and the thus-prepared dental prosthesis is then setting to the tooth by using a dental cement.

In the case of dental prostheses such as resin facing cast crowns or porcelain bonded facing cast crowns, these dental prostheses are prepared in a process in which a wax pattern of a core part is prepared on a plaster mold by using a wax in a lost wax casting method, the wax pattern is invested in a refractory investment, after curing the investment, the assembly is heated in an electric furnace to burn out the wax pattern, a metal is cast in a thus obtained mold, the resulting cast material is excavated from the investment, which is then cut and polished to prepare a metal core, and then, a hard resin for crown and bridge is built up and polymerized, or a porcelain is built up and burnt, in a core part of the thus obtained metal core.

In addition, in the case of dental prostheses such as ceramic inlays or all ceramic crowns, these dental prostheses are prepared in a process in which a duplicated model is prepared by using a refractory model material, a ceramic raw material is built up and burned on the thus-prepared duplicated model, the refractory duplicated model is eliminated, and then, trimming and polishing are then carried out.

However, in the case of a dental composite resin, since this process is one in which the dental composite resin in a paste-like form is polymerized for curing in the cavity, unpolymerized monomers inevitably remain, leading to a problem in pulp irritation.

In addition, in the case of dental prostheses, although as described above, complicated operations are required for the preparation of dental prostheses, this process is widely employed. However, since not only the shape in an oral cavity or the site in which a prosthesis is to be prepared is different individually, but also an extremely high precision in a several Atm order is required in the finished dental prosthesis, a skill of a dental technician along with a long period of time and a high cost is required.

Under these circumstances, as a method by which a dental prosthesis with a constant quality can be supplied within a short period of time and in a stable manner in recent years, a CAD/CAM system in which a dental prosthesis such as crowns or bridges is designed on a display by utilizing a computer has been drawing the attention, and a design and preparation system of dental prostheses by using such a CAD/CAM system represented by a Cerex system (by Siemens AG, Germany) is now commercially available. This system is a system in which a dental prosthesis is milling out of a ceramic block as a material to be grinded. However, according to this system, since the ceramic per se is hard, the finished dental prosthesis leads to a fear of likely wearing off the antagonistic enamel.

SUMMARY OF THE INVENTION

An object of the present invention is to provide a dental resin material having esthetics and mechanical properties suitable for dental prostheses such as inlays or crowns and free from unpolymerized monomers, which is superior in machinability and can be suitably used for the preparation of dental prostheses by milling processing by means of a CAD/CAM device and to provide a process for producing the same.

The present invention has been made by finding that while paying the attention to the fact that a dental composite resin is superior in esthetics and has mechanical properties, such as hardness, suitable for dental prostheses such as inlays or crowns and is free from wearing off the antagonistic enamel, when an acrylic resin polymer having the same composition as a dental composite resin, polymerized for curing under predetermined pressure and heating conditions is used as a material to be grinded, a dental prosthesis can be readily prepared by milling processing by means of a CAD/CAM device and that the thus obtained dental prosthesis is not only superior in esthetics and mechanical properties but also free from any fear of pulp irritation by unpolymerized monomers.

That is, the dental resin material according to the present invention is a dental resin material which is formed dental prosthesis by milling processing, comprising an acrylic resin polymer containing from 20 to 70% by weight of an inorganic filler having a mean particle size of from 0.01 to 0.04 $\mu$m in diameter. Also, the process for producing a dental resin material according to the present invention comprises polymerizing for curing a mixture comprising a combination of an inorganic filler having a mean particle size of from 0.01 to 0.04 $\mu$m in diameter, a methacrylate or acrylate monomer having at least one unsaturated double bond, and a heat polymerization initiator while elevating the pressure and heating under the conditions that the pressure is from 50 to 300 MPa and that the temperature is from 100 to 200° C., to thereby making it in a block form.

DETAILED DESCRIPTION OF THE INVENTION

In general, the dental composite resin is roughly classified into a hybrid type dental composite resin using a combination of a ultrafine inorganic filler having a mean particle size of from 0.01 to 0.04 $\mu$m in diameter and an inorganic filler having a relatively large particle size of from 0.1 to 5 $\mu$m in terms of the mean particle size in diameter and a dental composite resin using an organic-inorganic composite filler prepared by mixing, curing and pulverizing a mixture of a ultrafine inorganic filler having a mean particle size of from 0.01 to 0.04 $\mu$m in diameter and a monomer (the latter being generally abbreviated as "MFR"). The hybrid type dental composite resin is superior in mechanical properties but is inferior in surface lubricity and abrasion resistance. On the other hand, MFR is superior in surface lubricity and abrasion resistance but is inferior in mechanical properties.

In other words, the dental resin material according to the present invention is based on a hybrid type dental composite resin which has superior mechanical properties and comprises an acrylic resin polymer prepared by polymerizing for curing a combination of a methacrylate or acrylate monomer having at least one unsaturated double bond which is conventionally used for dental composite resins and a heat polymerization initiator, having from 20 to 70% by weight of an inorganic filler having a mean particle size of from 0.01 to 0.04 μm in diameter contained therein, while depressing the content of an inorganic filler having a mean particle size of from 0.1 to 5 μm in diameter as much as possible in order to impart superior surface lubricity and abrasion resistance.

Examples of methacrylate or acrylate monomers having at least one unsaturated double bond which can be used in the present invention include methyl methacrylate, ethyl methacrylate, isopropyl methacrylate, 2-hydroxyethyl methacrylate, 3-hydroxypropyl methacrylate, 2-hydroxy-1,3-dimethacryloxypropane, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, benzyl methacrylate, phenyl methacrylate, phenoxyethyl methacrylate, 2,2-bis(methacryloxyphenyl)propane, 2,2-bis[4-(2-hydroxy-3-methacryloxypropoxy)phenyl ] propane, 2,2-bis (4-methacryloxydiethoxyphenyl)propane, 2,2-bis(4-methacryloxypolyethoxyphenyl) propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1, 4-butandiol dimethacrylate, 1,6-hexanediol dimethacrylate, trimethylolpropane trimethacrylate, trimethylolethane trimethacrylate, pentaerythritol trimethacrylate, trimethylolmethane trimethacrylate, pentaerythritol tetramethacrylate, di-2-methacryloxyethyl -2,2,4-trimethylhexaethylene dicarbamate, 1,3,5-tris[1,3-bis(methacryloyloxy)-2-propoxycarbonyl-aminohexane ]-1,3,5-(1H, 3H, 5H)triazine-2,4,6-trione, and acrylates corresponding to these methacrylates. These methacrylates or acrylates can if required be used alone or in admixture.

As the heat polymerization initiator which can be used in the present invention, organic peroxides or azo compounds can be used. Specific examples include benzoyl peroxide, ketone peroxides, peroxy ketals, hydroperoxides, dialkyl peroxides, diacyl peroxides, peroxy esters, peroxy dicarbonates, 2,21-azobisisobutyronitrile, 2,21-azobis-2,4-dimethylvaleronitrile, 4,4'-azobis-4-cyanovaleric acid, 1,1'-azobis-1-cyclohexane carbonitrile, dimethyl-2,2'-azobisisobutyrate, and 2,2'-azobis-(2-aminopropane) dihydro-chloride. These compounds can be alone or in admixture.

As the inorganic filler having a mean particle size of from 0.01 to 0.04 μm in diameter which can be used in the present invention, collodial silica is generally used. Specific examples include Aerosil OX-50 (mean particle size: 0.04 μm in diameter) and Aerosil R-972 (mean particle size: 0.016 μm in diameter), both of which are made by Nippon Aerosil Co., Ltd. In case where the content of the inorganic filler having a mean particle size of from 0.01 to 0.04 μm in diameter is less than 20% by weight, a sufficient mechanical strength can not be obtained. On the other hand, if the content of the inorganic filler having a mean particle size of from 0.01 to 0.04 μm diameter exceeds 70% by weight, at the time of preparing a dental resin material, the resin paste is so hard that foams are likely contaminated into the resin polymer and hence, such is not suitable. Also, if the mean particle size of the inorganic filler is smaller than 0.01 μm in diameter, the inorganic filler is likely to coagulate so that it is hard to uniformly disperse the inorganic filler. On the other hand, if the mean particle size of the inorganic filler is larger than 0.04 μm in diameter, the surface lubricity tends to be lowered and hence, such is not suitable.

In case when the surface lubricity or abrasion resistance rather than the mechanical strength is required as in the case of use for simple inlays, depending upon the object for use, an organic-inorganic composite filler prepared by curing a mixture of the above-described ultrafine inorganic filler having a mean particle size of from 0.01 to 0.04 μm in diameter with the methacrylate or acrylate monomer having at least one unsaturated double bond and pulverizing the cured mixture so as to have a mean particle size of from 5 to 50 μm in diameter can be contained. At this time, a suitable content of the organic-inorganic composite filler which can be contained is from 1 to 40% by weight. If the content of the organic-inorganic composite filler is less than 1% by weight, an improving effect in the surface lubricity or abrasion resistance is not observed, whereas if it exceeds 40% by weight, the mechanical strength is lowered. On the other hand, in case where a high mechanical strength rather than the surface lubricity or abrasion resistance is required as in the case of posterior crowns, a glass powder having a mean particle size of from 0.1 to 5 μm in diameter can be further contained. In this case, a suitable amount of the glass powder which can be contained is from 1 to 40% by weight. If the content of the glass powder is less than 1% by weight, an improving effect in the mechanical strength is not observed, whereas if it exceeds 40% by weight, the surface lubricity is lowered. While the composition of the glass powder is not particularly limited, suitable examples of the glass powder which can be contained include quartz glass, alumino silicate glass, glasses containing an alkaline earth metal atom (such as calcium, strontium, and barium) and having X-ray contrast properties, zinc glass, and lead glass. It is desired that the surface of the glass powder is subjected to a silane-modified. Usually, organosilicon compounds such as γ-methacryloxypropyl trimethoxysilane, having been converted into a silane by a customary manner, are used as the surface treatment agent.

Besides, the dental resin material according to the present invention can contain slight amounts of ultraviolet light absorbers, coloring agents, polymerization inhibitors, and the like, if desired.

The dental resin material comprising the above-described constitutional components according to the present invention is, after compounding, poured into a mold, is pressurized at from 50 to 300 MPa, is polymerized for curing upon heating at from 100 to 200° C., and is then molded into a block-like shape. By heat polymerization under an elevated pressure, a complete polymer which is free from contamination of foams and in which no unpolymerized monomers remain can be obtained. If the pressure is less than 50 MPa, the contamination of foams can not be sufficiently inhibited, whereas even if it exceeds 300 MPa, any further improving effect is not observed, but it is rather difficult to keep such a high pressure. In addition, if the heating temperature is lower than 100° C., unpolymerized monomers likely remain, or it takes a long period of time to undergo the polymerization, and hence, such is not suitable. On the other hand, if the heating temperature exceeds 200° C., it is difficult to control the temperature, and hence, such is not suitable, neither.

Accordingly, it is suitable that the dental resin material according to the present invention is prepared in a block-like shape by undergoing the polymerization for curing upon heating at from 100 to 200° C. under an elevated pressure of from 50 to 300 MPa. The polymerization for curing is usually carried out while keeping the heating state under an elevated pressure for about 10 to 30 minutes, depending upon the size of the block.

The shape of the block is usually of a rectangular parallelopiped or a cylinder. It is preferred that the shape is previously made similar to an inlay or a crown. This is because the grinding amount at the time of milling processing can be depressed to a small amount.

Thus, in order to prepare a dental prosthesis by using the dental resin material according to the present invention, impressions at the abutment tooth side and the antagonistic side in the oral cavity of a patient are first taken by using a dental impression material. At the time of impression taking of maxilla and mandibule, the impression taking can be carried out simultaneously or individually for the maxilla and the mandibule. A plaster model is prepared based on the thus taken impressions. Then, the plaster model is measured by means of a contact-type or non-contact-type measuring instrument to obtain a three-dimensional coordinate data with respect to the shape in the oral cavity, which is then accumulated in a memory in a computer as a digital signal. Thereafter, using the three-dimensional coordinate data accumulated in the memory, an abutment tooth shape of a patient is graphically displayed on CRT (Cathode Ray Tube) by means of a wire frame or the like. The relative position with respect to an antagonistic tooth is graphically reproduced on a CRT by previously providing a certain reference point on a plaster model for each of the maxilla and the mandibule and making the respective reference points fit to each other, using a data measured for the shape of the maxilla as well as a data measured for the shape of the mandibule.

Then, a form of an inlay or a crown is plotted and designed on a basis of the abutment tooth shape and the shape of the antagonistic tooth graphically displayed on the CRT. In this case, it is possible to make the design more easily by using a previously registered standard data for inlays or crowns. In addition, if desired, an offset with an arbitrary dimension can be provided inside the inlay or crown, thereby produce a cement space. Thus, when the design for inlays or crowns has been finished to obtain the three-dimensional coordinate data, a processing command is transmitted from the computer to an NC (numerical control) processing machine, thereby subjecting a dental resin material in a block-like shape to milling processing to produce inlays or crowns. In addition, if desired, in order to adjust the shade with remaining teeth of a patient, characterization such as stain can be effected by using a composite resin for crown and bridge.

The dental resin material and the process for producing the same according to the present invention will be hereunder explained with reference to the following Examples.

EXAMPLE 1

27% by weight of di-2-methacryloxy-2,2,4-trimethylhexamethylene dicarbamate (hereinafter referred to as "UDMA") and 8% by weight of a mixture comprising 1,6-methacrylethyloxycarbonylaminohexane, 1,3-methacrylethyl-oxycarbonylaminohexyl aminocarbonyloxy (3-methyl)propane, and 1,6-methacrylethyloxycarbonylaminohexyl amino-carbonyloxy (3-methyl)propyloxycarbonylaminohexane, which is represented by the following structural formula:

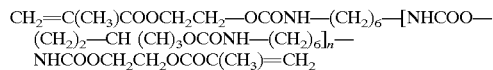

wherein n is from 0 to 2,
[a trade name "Art Resin SH-101", made by Negami Kogyo K.K. (hereinafter referred to as "SH-101")] as a methacrylate or acrylate monomer having at least one unsaturated double bond; 0.5 part by weight (based on 100 parts by weight of the sum of UDMA and SH-101) of benzoyl peroxide as a heat polymerization initiator; and 65% by weight of a powder obtained by surface-processing colloidal silica having a mean particle size of 0.04 μm (a trade name "Aerosil OX-50", made by Nippon Aerosil Co., Ltd.), which had been surface-modified with 10 parts by weight of γ-methacryloxypropyl trimethoxysilane as an inorganic filler were compounded and kneaded in a kneader to obtain a paste.

This paste was charged into a mold having an inner diameter of 15 mm and a height of 25 mm and heat polymerized while keeping at 150° C. for 15 minutes under a pressure of 100 MPa by using a heat press. After cooling, the polymerization product was taken out from the mold to produce a cylindrical dental resin material. The thus produced dental resin material was subjected to comparison testing for the respective items as described below. The results obtained are shown in Table 1.

[Test Items]
(1) Bending Strength Test

A specimen having a size of 2 mm×2 mm×25 mm was cut out from the dental resin material as produced, immersed in distilled water at 37° C. for 24 hours, and then subjected to a three-point bending test with a span of 20 mm at a crosshead speed of 1 mm/min by means of Autograph (made by Shimadzu Corporation).
(2) Ten-Point Mean Roughness Test A specimen having a diameter of 15 mm and a thickness of 2 mm was cut out from the dental resin material as produced, polished with an emery paper #600, and further polished successively with a water paste of a prosthodontic polishing sand (fine) and a water paste of finishing alumina (0.3 μm). Then, the ten-point mean roughness was measured by means of a surface roughness tester (made by Kosaka Kenkyusho K.K.).
(3) Compressive Abrasion Test A conical specimen having a height of 5 mm [basal portion: 6 mm in diameter×2 mm in height; test surface portion (upper portion): 2.1 mm in diameter×1 mm in height; intermediate portion (transitional portion): 2 mm in height] was cut out from the dental resin material as produced and immersed in distilled water at 37° C. for 24 hours. Thereafter, the specimen was installed in an abrasion tester, reciprocally moved on emery papers (#600 and #1000) to obtain parallel surfaces of a basal surface and a test surface. Then, the specimen was once taken out from the abrasion tester, the basal portion of which was then covered by a silicone impression material, followed by immersing in a 0.1N-NaOH aqueous solution at 37° C. for 6 days. Subsequently, the specimen was washed with distilled water, measured for its height by means of a micrometer, and again installed in the abrasion tester. A polishing material comprising a spherical powder of polymethyl methacrylate (not larger 250 μm) and glycerin (1/1 (W/V)) was poured on a scratch polishing cloth on the paraplates, and the specimen was subjected to compressive sliding motion under a load of 0.87 MPa at a rate of 130 times per minute in 100,000 cycles in which one cycle was comprised of one-time vertical motion and subsequent reciprocal motion (sliding distance: 25 mm). After testing, the height of the specimen was measured, and a difference before and after the test was taken as an abrasion amount.

(4) Amount Of Unpolymerized Monomer

A thin piece having a thickness of 0.15 +0.025 mm was cut out from the dental resin material as produced, measured for its weight, and then immersed on 100% methanol (5 ml) as an eluting solution for 24 hours. Thereafter, the eluting solution was added with 5 ml of ethanol containing 2-ethylhexyl methacrylate as an internal standard sample, and the amount of the monomer was measured by means of a high-performance liquid chromatography (HPLC). Then, the amount of the unpolymerized monomer was calculated from the calibration curve, and a proportion against the weight before the immersion was shown.

EXAMPLES 2 TO 5 AND COMPARATIVE EXAMPLE 1

Dental resin materials were produced in the same manner as in Example 1, except for changing the compounding ratio to ones as shown in Table 1 (however, in Example 2, 2,2'-azobisisobutyronitrile was used as the heat polymerization initiator), and then subjected to the respective tests. The results obtained are shown in Table 1.

Incidentally, as the organic-inorganic composite filler used in Example 2 and Comparative Example 1, a powder obtained by heat polymerizing a mixture of 45% by weight of colloidal silica having a mean particle size of 0.04 μm in diameter (a trade name "Aerosil OX-50", made by Nippon Aerosil Co., Ltd.), which had been surface-modified with 10 parts by weight of γ-methacryloxypropyl trimethoxysilane in a customary manner, and 55% by weight of a solution comprising 100 parts by weight of a monomer mixed solution comprising 19 parts by weight of UDMA, 13 parts by weight of 1,3,5-tris[1,3-bis(methacryloyloxy)-2-propoxycarbonyl-aminohexane]-1,3,5-(lH, 3H, 5H 2,4,6-trione (hereinafter referred to as "U-6H"), and 13 parts by weight of neopentyl glycol dimethacrylate (hereinafter referred to as "NPG"), having 1 part by weight of 2,2'-azobisisobutyronitrile dissolved therein, these components were mixed and heat-cured followed by pulverizing to obtain powders having a mean particle size of 10 μm in diameter was used.

COMPARATIVE EXAMPLE 2

A commercially available dental photo-polymerization type composite resin which is used for restoration by direct filling was tested in the same manner as in Example 1. Incidentally, the test samples were produced by filling the dental resin composite in each of molds for preparing a specimen dependent on the respective tests and irradiating it with a light in a photo-polymerization vessel (a trade name "LABOLIGHT LV-II", made by GC Corporation) for 5 minutes, thereby undergoing hardening.

TABLE 1

| | Composition | | | | Mechanical Properties | | | |
|---|---|---|---|---|---|---|---|---|
| | | | Organic-inorganic | | | | | |
| | Monomer (% by weight) | Inorganic Filter (% by weight) | Composite Filter (% by weight) | Glass Powder (% by weight) | Bending Strength (MPa) | Ten-point Mean Roughness (μm) | Amount of compressive Abrasion (μm) | Amount of Unpolymerized Monomer (%) |
| Example 1 | UDMA 27<br>SH-101 8 | 65 | — | — | 190 | 0.19 | 1.8 | Not detected |
| Example 2 | UDMA 24<br>SH-101 8 | 38 | 30 | — | 150 | 0.22 | 5.2 | Not detected |
| Example 3 | UDMA 16<br>SH-101 5<br>BG[1)] 4 | 45 | — | Aluminosilicate glass powder (mean particle size: 1.0 μm) 30 | 214 | 0.34 | 23.0 | Not detected |
| Example 4 | UDMA 18<br>SH-101 5<br>BG 5 | 52 | — | Barium glass powder (mean particle size: 0.5 μm) 20 | 212 | 0.25 | 15.0 | Not detected |
| Example 5 | UDMA 5<br>Bis-MEPP[2)] 20 | 22 | — | Quartz glass powder (mean particle size: 0.5 μm) 23<br>Barium glass powder (mean particle size: 0.5 um) 30 | 193 | 0.27 | 29.0 | Not detected |
| Comparative Example 1 | UDMA 25<br>SH-101 8 | — | 67 | — | 96 | 0.23 | 10.0 | Not detected |
| Comparative Example 2 | Commercially available photo-polymerization type composite resin [a trade name "Graft LCII", made by GC Corporation | | | | 151 | 1.20 | 37.0 | 0.96 |

(Note)
[1)]BG: 1,3-Butanediol dimethacrylate
[2)]Bis-MEPP: 2,2-Bis(4-methacryloxyethoxyphenyl)propane As is clear from Table 1, it can be confirmed that the dental resin materials of the respective Examples are superior in mechanical properties and are free from any unpolymerized monomer and hence, can be used as inlays or crowns without anxiety, as compared with those of the Comparative Examples. In addition, as a result of actually producing crowns for posterior teeth by using the dental resin materials of the respective Examples by milling processing by means of a CAD/CAM device, crowns could be easily produced within a shorter period of time with good milling processability in any dental resin materials of the Examples. Also, when the crowns were setting in an oral cavity, they neither caused pulp irritation by the unpolymerized monomer nor wore the antagonistic enamel and were superior in surface lubricity and abrasion resistance.

In the light of the above, the dental resin material according to the present invention can be properly used for the preparation of dental prostheses such as inlays or crowns in milling processing by means of a CAD/CAM device. Also, the resulting dental prostheses are not only superior in esthetics but also exhibit proper mechanical properties as inlays or crowns. Thus, the dental resin material according to the present invention greatly contributes to the dental medical field.

While the invention has been described in detail and with reference to specific embodiments thereof, it will be apparent to one skilled in the art that various changes and modifications can be made therein without departing from the spirit and scope thereof.

What is claimed is:

1. A process for producing a dental resin material which comprises polymerizing for curing a mixture comprising a combination of from 20 to 70% by weight of an inorganic filler having a mean particle size of from 0.01 to 0.04 μm in diameter, a methacrylate or acrylate monomer having at least one unsaturated double bond, and a heat polymerization initiator while elevating the pressure and heating under the conditions that the pressure is from 50 to 300 MPa and that the temperature is from 100 to 200° C.

2. A process for producing a dental resin material as claimed in claim 1, in which the mixture further comprises from 1 to 40% by weight of a glass powder having a mean particle size of from 0.1 to 5 μm in diameter.

3. A process for producing a dental resin material as claimed in claim 1, in which the mixture further comprises from 1 to 40% by weight of an organic-inorganic composite filler prepared by mixing and curing a mixture of a ultrafine inorganic filler having a mean particle size of from 0.01 to 0.04 μm in diameter with a methacrylate or acrylate monomer having at least one unsaturated double bond and pulverizing the cured mixture so as to have a mean particle size of from 5 to 50 μm in diameter.

4. A process for producing a dental resin material as claimed in claim 2, in which the mixture further comprises from 1 to 40% by weight of an organic-inorganic composite filler prepared by mixing and curing a mixture of a ultrafine inorganic filler having a mean particle size of from 0.01 to 0.04 μm in diameter with a methacrylate or acrylate monomer having at least one unsaturated double bond and pulverizing the cured mixture so as to have a mean particle size of from 5 to 50 μm in diameter.

5. The dental resin material produced by the process of claim 1.

6. The dental resin material produced by the process of claim 2.

7. The dental resin material produced by the process of claim 3.

8. The dental resin material produced by the process of claim 4.

* * * * *